United States Patent [19]

Lazarus et al.

[11] Patent Number: 4,479,792
[45] Date of Patent: Oct. 30, 1984

[54] PERITONEAL FLUID TREATMENT APPARATUS, PACKAGE AND METHOD

[76] Inventors: Harrison Lazarus, 843 13th Ave., Salt Lake City, Utah 84103; James A. Nelson, 1708 Forest Hills Dr., Salt Lake City, Utah 84106

[21] Appl. No.: 423,034

[22] Filed: Sep. 24, 1982

Related U.S. Application Data

[60] Continuation of Ser. No. 181,219, Aug. 22, 1980, Pat. No. 4,351,333, which is a continuation of Ser. No. 945,525, Sep. 25, 1978, abandoned, which is a division of Ser. No. 722,752, Sep. 13, 1976, Pat. No. 4,128,173, which is a continuation of Ser. No. 626,323, Oct. 28, 1975, abandoned.

[51] Int. Cl.³ .......................................... A61M 25/00
[52] U.S. Cl. ...................................... 604/29; 128/656
[58] Field of Search .................. 604/29, 164; 128/654, 128/656, 658, 753, 754

[56] References Cited

U.S. PATENT DOCUMENTS

| | | | |
|---|---|---|---|
| 3,352,306 | 11/1967 | Hirsch | 604/164 |
| 3,459,188 | 8/1969 | Roberts | 604/164 |
| 3,520,298 | 7/1970 | Lange | 604/29 |
| 3,547,103 | 12/1970 | Cook | 604/29 |
| 3,698,396 | 10/1972 | Katerndahl et al. | 604/164 |
| 3,730,183 | 5/1973 | Goldsmith et al. | 604/164 |
| 3,941,119 | 3/1976 | Corrales | 604/29 |

FOREIGN PATENT DOCUMENTS

2105453   8/1971   Fed. Rep. of Germany ...... 604/164

OTHER PUBLICATIONS

Weston et al., "Stylet-Catheter for Peritoneal Dialysis" Lancet, pp. 1047-1049, May 15, 1965.
Parvin et al., "Effectiveness of Peritoneal Lavage in Blunt Abdominal Trauma, Anal of Surgery, Mar. 1975.
Perry, Jr. et al., "Diagnostic Peritoneal Lavage in Blunt Abdominal Trauma, vol. 71 #6, Jun. 1972, Surgery.
Seldinger, "Catheter Replacement of the Needle in Percutaneous Arteriography", Oct. 1952.
Lazarus et al., "Peritoneal Lavage with Low Morbidity", Jacep, Aug. 1979.
Fischer et al., "Diagnostic Peritoneal Lavage" AM, Journal of Surgery vol. 136, pp. 701-704, 1978.
Hornyak et al., "Value of Inconclusive Lavage in Abdominal Trauma", Journal of Trauma, May 1979.

*Primary Examiner*—John D. Yasko
*Attorney, Agent, or Firm*—Trask & Britt

[57] ABSTRACT

The cannula of a conventional intravascular catheter is placed into the peritoneal cavity through a small shallow incision in antiseptically prepared skin. The stylet or trocar of the conventional catheter is removed; and a stainless steel elongated flexible guide is inserted through the catheter's cannula into the peritoneal cavity. The catheter's cannula is removed and a flexible elongated cannula inserted into the cavity over the guide and secured in place with a suture. Fluid operation means is connected to the elongated cannula by connector means to permit fluid treatment after removal of the guide. Apparatus to effect peritoneal fluid treatment are placed in sterile openable sealed packages for storage and transport.

6 Claims, 8 Drawing Figures

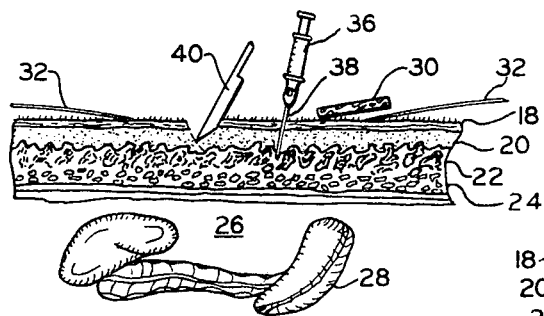
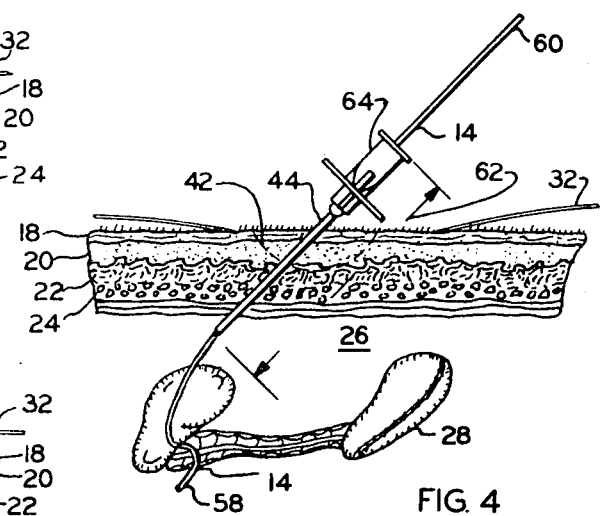
FIG. 2
FIG. 4
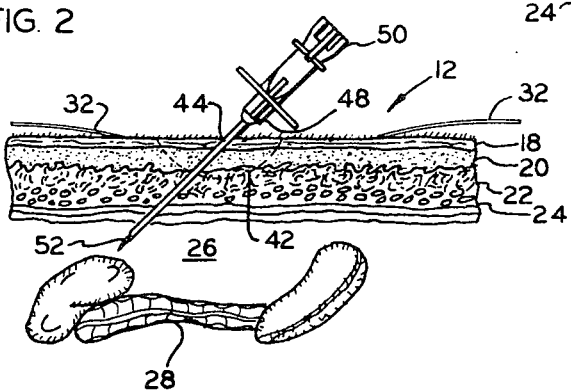
FIG. 3A
FIG. 3B
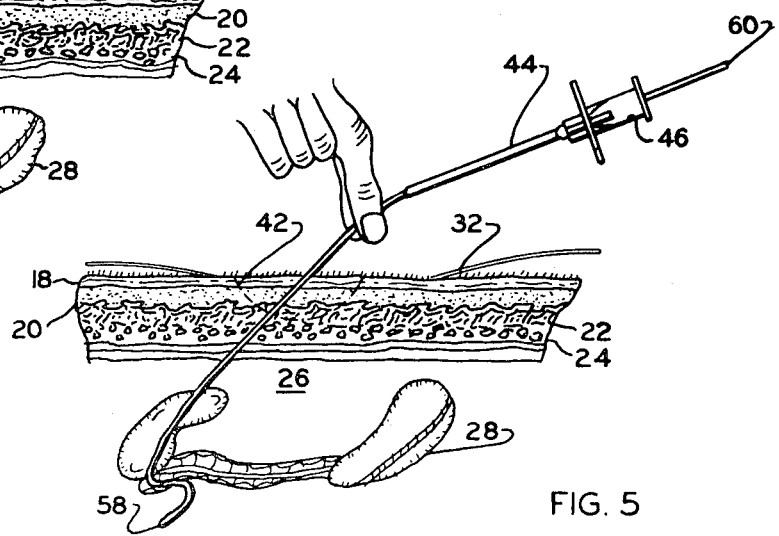
FIG. 5

PERITONEAL FLUID TREATMENT APPARATUS, PACKAGE AND METHOD

This application is a continuation of application Ser. No. 181,219 filed Aug. 22, 1980, now U.S. Pat. No. 4,351,333; which patent is a continuation of application Ser. No. 945,525 filed Sept. 25, 1978, now abandoned; which application is a divisional of application Ser. No. 722,752 filed Sept. 13, 1976, now U.S. Pat. No. 4,128,173; which patent is a continuation of application Ser. No. 626,323 filed Oct. 28, 1975, now abandoned.

BACKGROUND OF THE INVENTION

1. Field

This invention relates to medical apparatus to be used in peritoneal cavity treatment. More particularly, this invention discloses apparatus, a package and method for extracting from and introducing fluids into the peritoneal cavity.

2. State of the Art

Fluid treatment involving the peritoneal cavity and its related viscera include peritoneal aspiration, peritoneal lavage, peritoneal dialysis and drainage of voidable viscus. These treatments are well known and are typically regarded as effective techniques for diagnosis and/or treatment of peritoneal trauma and more particularly blunt abdominal trauma. See, e.g.; Root, H. D., Hauser, C. W., McKinley, C. R., LaFava, J. W., Mendiola, Jr., R. P., "Diagnostic Peritoneal Lavage," *Surgery,* (MAY 1965), pp. 633–637; c.f., Gill, W., Champion, H. R., Long, W. B., Jamaris, J., Cowley, R. A., "Abdominal Lavage in Blunt Trauma," *Br. J. Surg.,* Vol. 62 (1975), pp. 121–124. Peritoneal fluid treatment is also useful for diagnosing ectopic pregnancy, mesenteric thrombosis, splenic infarction and other intra-abdominal maladies which could display as symptoms intra-abdominal hemorrhage or result in the presence of other detectable fluids in the peritoneal cavity. See, Jahadi, M. R., "Diagnostic Peritoneal Lavage," *The Journal of Trauma, (November* 1972). pp. 936–938.

Initially, a trocar with a multiple side hole dialysis cannula was suggested to effect the peritoneal fluid treatment above described. Root et al, supra. Subsequently, a peritoneal catheter comprised of an outside-the-needle multiple hole cannula with an internal removable trocar was suggested and used. Perry, Jr., J. F., Strate, R. G., "Diagnostic Peritoneal Lavage in Blunt Abdominal Trauma: Indication and Results," *Surgery,* June 1972), pp. 898–901; c.f., Thal, E. R., Shires, G. T., "Peritoneal Lavage in Blunt Abdominal Trauma," *The American Journal of Surgery,* Vol. 125 (January 1973), pp. 64–69; Jahadi, supra. A STYLO-CATH with L-connector (Number 4711) which is made by Abbot Laboratories is one of these devices.

Use of the peritoneal catheter such as the STYLO-CATH in the course of peritoneal fluid treatment resulted in further trauma to the patient in a noticeable number of cases. For example, small and large bowel perforations, mesentery vessel puncture and retroperitoneal hematomas have been caused. A rectus abdominis injury and a perforation of the left iliac artery have also been observed as a direct result of treatment with peritoneal dialysis catheters.

To avoid inducing such trauma some have reported using an incision of some length and depth into the subcutaneous tissue followed by an insertion of the peritoneal dialysis catheter. Such incisions are undesirable because they increase the risk of infection, wound separation and wound hematoma. E.g., Parvin, S., Smith. D. E., Asher, W. M., Virgilio, R. W., "Effectiveness of Peritoneal Lavage in Blunt Abdominal Trauma," *Ann. Surg.,* (March 1975), pp. 255–261. Incisions through the peritoneum or deep incisions which result in accidental laceration of the peritoneum are similarly not desirable and additionally may result in leakage of blood from the subcutaneous area into the peritoneal cavity. Such leakage may result in improper diagnosis.

Blunt abdominal trauma is typically diagnosed under emergency conditions in an emergency room of a hospital. Speed in diagnosis is important so that repairs to damaged organs can be swiftly effected to minimize the well known mortality rates associated with such injuries. Peritoneal fluid treatment apparatus heretofore known is typically an aggregation of various apparatus and materials. As a result, valuable time may be lost in collecting the necessary materials and apparatus to effect treatment.

From the above, it can be seen that a need exists for peritoneal fluid treatment methods and apparatus which do not expose the patient to further trauma and the subsequent complications which result therefrom. Further, there is a need for prepositioning the materials and apparatus required to effect treatment.

SUMMARY OF THE INVENTION

The peritoneal fluid treatment apparatus of this invention includes a conventional intravascular catheter of the type having a cannula and a stylet or trocar. The cannula is insertable into the peritoneal cavity. Flexible elongated guide means is sized to fit through the catheter cannula into the peritoneal cavity. A second elongated cannula is flexible and sized to fit over the guide means into the peritoneal cavity. Connector means are adapted to the end of the second cannula external to the body for connection to peritoneal fluid operation means after removal of the guide means.

In another embodiment of the invention the guide means is an elongated refractory metal wire which may be a spring-wound type stainless steel wire having a highly flexible portion and a less flexible portion. The second cannula may be a flexible plastic-like tube tapered on the end opposite the connector means to fit slideably and snuggly about the guide means. The second cannula may also have a plurality of apertures formed therein along a portion of its length from the tapered end toward the connector means.

Also disclosed is a method for peritoneal fluid treatment wherein a patch of skin about the peritoneum is sterilized. A small shallow incision or nick is made in the sterilized skin through which an intravascular catheter of the type having a removable stylet or trocar is inserted into the peritoneal cavity. Thereafter, the stylet or trocar is removed and guide means inserted into the peritoneal cavity through the cannula of the catheter which is thereafter removed. Then a second cannula, is inserted into the cavity over the guide means which is thereafter removed. The second cannula may be secured in place with a suture. Fluid operation means is then connected by connector means to the second cannula.

Also disclosed is a package which contains apparatus and materials for practicing methods of the type herein disclosed.

BRIEF DESCRIPTION OF THE DRAWINGS

In the drawings, which illustrate the best mode presently contemplated for carrying out the invention, FIGS. 2 through 7 are partial cross-sectional views of the body in the vicinity of the peritoneal cavity and side views of apparatus of the invention illustrating the sequence of apparatus operations.

DESCRIPTION OF THE ILLUSTRATED EMBODIMENT

Figure 1:
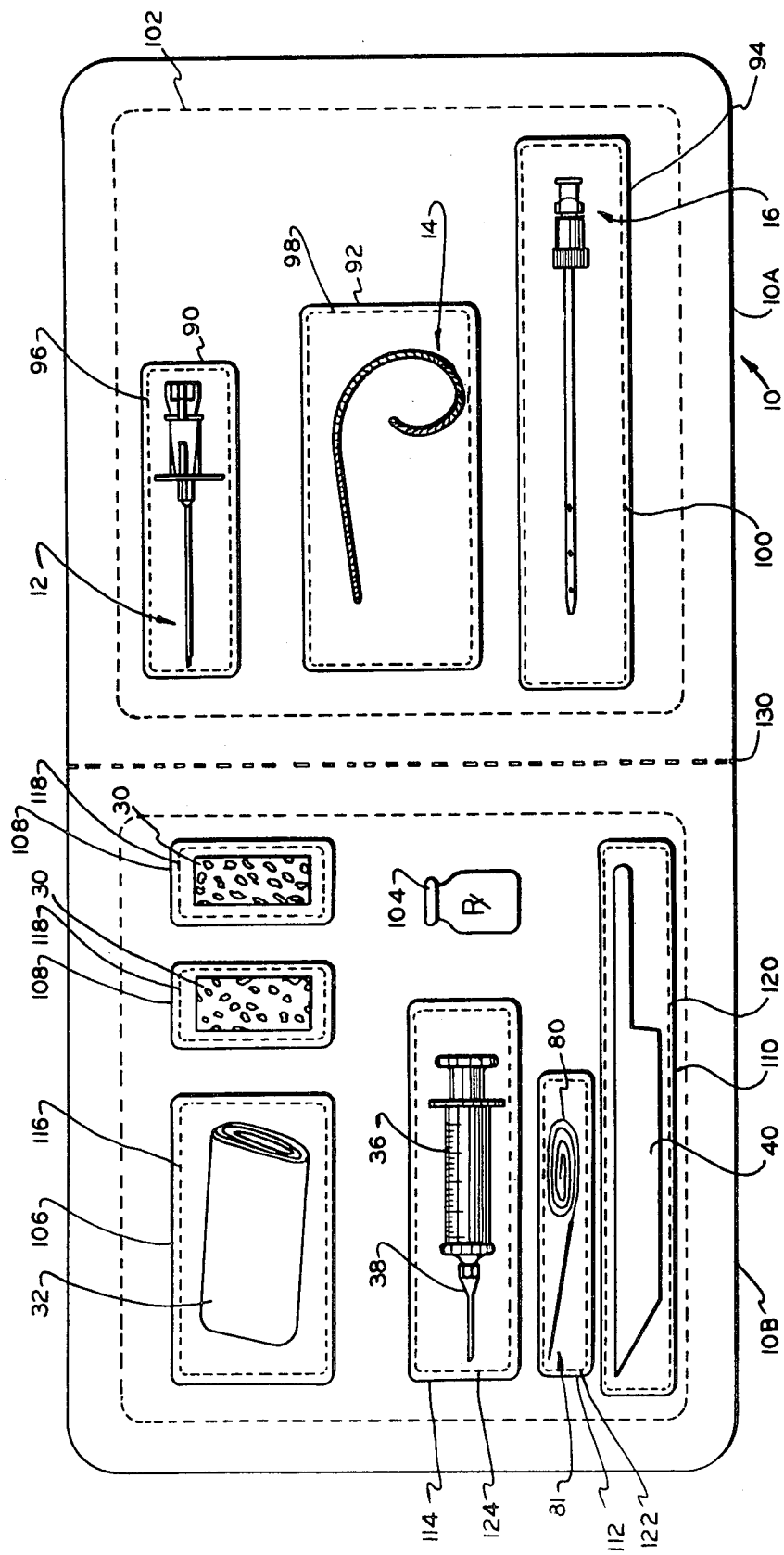
FIG. 1 is a cut-away top view illustrating packages and apparatus of the invention.

FIG. 1 illustrates a package 10 containing a conventional intravascular catheter 12, a wire guide 14 constituting guide means, and an elongated cannula 16. The package 10 may also contain other materials as more fully discussed hereinafter.

FIGS. 2 through 6 depict the apparatus of the presently preferred embodiment of the invention in the preferred sequence of use. The cross-sectional side view of a portion of the body in FIGS. 2 through 6 shows the surface of the skin 18, the underlying layers of skin 20, the subcutaneous area 22, the peritoneum 24 and the peritoneal cavity 26 containing various body organs 28.

Referring in particular to FIG. 2, it can be seen that the patient under treatment is placed in a generally supine orientation. However, other factors (e.g., other injuries) may dictate positioning the patient differently. A small area or patch of the surface of the skin 18 (e.g., 10 cm × 10 cm) is prepared by cleaning it with an antiseptic agent which is preferably contained in sponge 30, which together constitute skin preparation means. The site of the small area or patch is preferably on the front of the body just below the navel, though it may be at any location which allows access to the peritoneal cavity 26. After cleaning, a body drape 32 is preferably placed over the patient and an aperture formed desirably conforming in contour and shape but smaller in dimension than the patch of the prepared skin surface 18. The aperture of the drape 32 is aligned to leave exposed prepared skin surface 18.

After installation of the drape 32, it is preferred to administer a local anesthetic to the skin area to minimize patient discomfort. Local anesthetic means as here illustrated is a local anesthetic (e.g., procaine) in a 2 to 5 milliliter syringe 36 having a 26 gauge needle 38. Those skilled in the art, however, will recognize that other syringes, needles and anesthetics are also adaptable for such purpose. Those skilled in the art will also recognize that a local anesthetic may not be required for an unconscious, sedated or otherwise unfeeling patient.

After administering the local anesthetic to the exposed prepared skin surface 18, it is preferred to make a short and shallow incision through the skin 20 and into the subcutaneous area 22. The incision 42 is desirably made with a standard number 11 size surgical knife 40. The incision 42 is preferably about 2 to 5 millimeters deep and about 2 to 5 millimeters long for a normal adult patient. The incision 42 is in reality a nick in the skin 18 sufficient to permit passage of the catheter 12 and second cannula 16. In practice, it has been found that the length of the incision need only be slightly longer (e.g., 1 millimeter) than the diameter of the second cannula 16. Care should be taken to not penetrate through the subcutaneous area 22 and lacerate the peritoneum 24. It may be noted that the incision illustrated by the dotted line 42 in FIGS. 2 through 6 is not to scale and not proportionally reflective of the preferred dimensions.

Upon completion of the preparatory steps above described, the intravascular catheter 12 is inserted through the incision 42 and peritoneum 24 into the peritoneal cavity 26 as illustrated in FIG. 3a and b. The intravascular catheter 12 is a conventional outside-the-needle catheter of the type described and illustrated in U.S. Pat. No. 3,352,306 (Hirsch). It has a cannula 44 affixed to a hub 46 and a trocar or stylet 48 removably positioned therewithin. The trocar or stylet 48, which constitutes needle means, has handle means 50 on one end and a sharpened point 52 at its other end which extends slightly beyond the cannula 44 when positioned in the cannula 44 and hub 46. The cannula 44 is preferably of relatively small diameter (e.g., 0.5 to about 1.5 millimeters) and moderate length (e.g., 4 centimeters to about 10 centimeters). The trocar or stylet 48 is sized to cooperate with the hub 46 and cannula 44 in a well known fashion as illustrated in FIGS. 1 and 3a. Catheters having substantially smaller diameter cannulae than as above-described are useable but not desired because the guide means hereinafter described and discussed is concomitantly restricted in size and in turn effectiveness. Catheters having substantially larger diameter cannulae are not desired because of the potential hazard or threat they pose to the organs 28 in the peritoneal cavity 26 and to the peritoneum 24 itself. In particular, penetration of the peritoneum 24, by a large diameter cannula with a similarly large trocar or stylet 48, may result in a tear in the peritoneum which may require surgical repair. Such a tear may also allow blood to enter the cavity 26 which may invalidate a diagnosis resulting from the indications obtained through the fluid treatment. A large stylet or trocar with cannula poses a similar threat to the organs 28 in the peritoneal cavity 26.

Catheters having cannulae which are shorter or longer are similarly not desirable. If a catheter is too short, it may not be long enough to penetrate the peritoneum 24. If it is too long it will extend too far into the cavity 26. With the stylet or trocar point 52 extending beyond the cannula 44 and in the dynamics of insertion, it can be seen that the probability of inflicting a laceration, tear or large diameter puncture to an internal organ with the catheter 12 is significantly increased. Such a laceration, tear or puncture may necessarily require rather immediate surgical repair when the patient may be suffering from other trauma or injury so that risk to life is notably present. It is recognized, however, that for very obese patients, a catheter 12 somewhat longer than above-described may be preferred. Nevertheless, it has been found that the dimensional characteristics above-described are highly preferred for almost all adolescent and adult patients.

Although a variety of conventional outside-the-needle catheters having the above-described characteristics may be used, it has been found that a catheter of the type having a rigid cannula made of a refractory metal such as stainless steel is preferred. A Becton-Dickinson 18G23/4 thin wall catheter (reorder No. 8270) using a Potts-Cournand needle is such a catheter and is acceptable for most applications.

The insertion of the catheter 12 into the peritoneal cavity 26 must be effected with care to avoid contaminating the catheter 12 with blood from subcutaneous tissue 22 about the incision 42. Also one must avoid tearing the subcutaneous tissue 22 and peritoneum 24 so that blood from the incision 42 will not drain into the cavity 26. Further, the possibility still exists, though substantially less than with methods and apparatus known in the art, that an organ 28 could be lacerated by the point 50 of the trocar or stylet 48. If inserted carefully and slowly, the user can feel the change in resistance (force required to advance) when an organ 28 is confronted by the point 50 and stop advancement or change direction of advancement. In the past, with apparatus inserted deep into the cavity 26, the resistance would vary so much as organs were touched or pushed aside that one could not readily guard against accidental perforations and lacerations.

It should be noted that the catheter 12 can be inserted at almost any angle and in any direction. For supine patients, it is preferred to insert the catheter 12 at about 5° from the vertical pointed toward the pelvic region on a body centerline with the navel with the point of insertion being on the centerline below the navel.

After the catheter 12 is inserted and the cannula 44 positioned to extend into the cavity 26, the stylet or trocar 48 is withdrawn leaving the cannula 44 in place as shown in FIG. 3b.

With the stylet or trocar 48 removed, the guide means 14 is inserted through the hub 46 and cannula 44 into the peritoneal cavity 26. The guide means 14 is an elongated wire-like device dimensioned in cross-section (e.g., from about 0.5 to about 2 millimeters) to fit within the hub 46 and cannula 44 of the catheter 12 and in length to be substantially longer than the cannula 44. Preferably the guide means 14 is sized in length to be at least about three times the overall axial length of the cannula 44 and hub 46 (e.g., from about 20 to 50 centimeters in length). The guide means 14 should have some axial rigidity to permit it to be easily advanced (inserted) while having sufficient flexibility to bend and flex around internal organs 28 as it is advanced. The advanced end 58 is blunt to further reduce the chance of damaging the organs 28. It has been found that a highly preferred guide means 1, is very flexible from the inserted end 58 to a point about midway along its length and thereafter less flexible or somewhat stiff to the external end 60 of the guide means 14. It has also been found that a highly preferred guide means 14 is constructed of a refractory metal such as stainless steel in a spring wound fashion similar to a piano wire. A Cook Incorporated Wire Guide, type SFNA, 30 centimeters in length, has been found to be suitable as the guide means 14.

The wire guide 14 is advanced into the peritoneal cavity 26 until about one catheter length (length of cannula 44 plus hub 46) 62 of guide means 14 remains between the top of the hub 64 and the external end 60 of the guide means 14. The blunt end 58 of the guide means 14 is thus advanced well into the cavity 26 in between the organs 28. Thereupon the cannula 44 and hub 46 are removed over the guide means 14 leaving the guide means 14 inserted through the incision 42 and in the peritoneal cavity 26 as illustrated in FIG. 5.

Figures 6, 7:
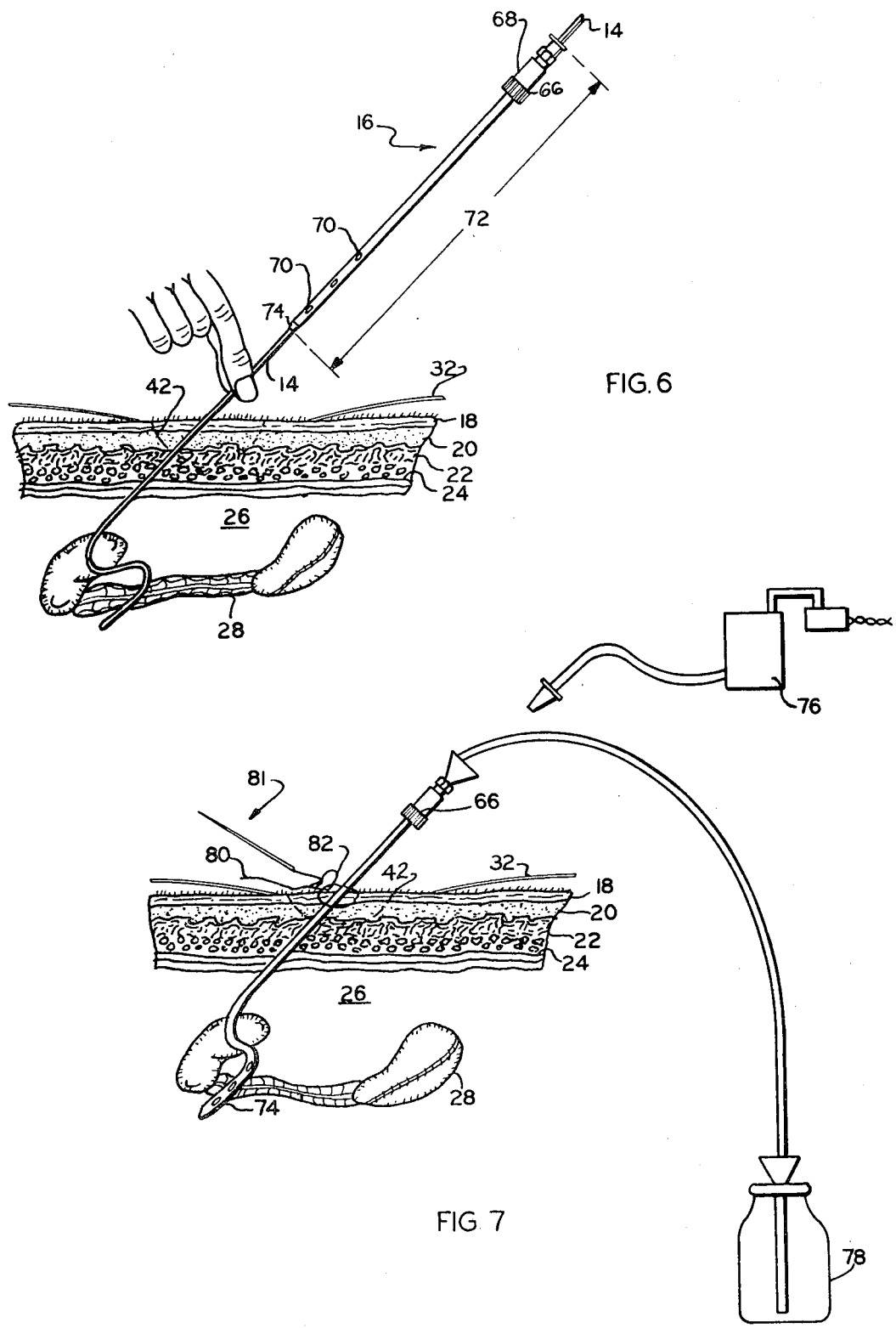

When the cannula 44 and hub 46 are removed, the elongated cannula 16 is threaded over the guide means 14 as depicted in FIG. 6. The elongated cannula 16 is flexible with connector means 66 secured to its external end 68 for connection as hereinafter described. A plurality of apertures 70 (e.g., about 6) along the length 72 of the cannula 16 from the tip 74 positioned in the cavity 26 to a point from about ⅓ to midway along the length 72 of the cannula 16. Positioning of the apertures 70 farther along the length 72 of the cannula 16 (i.e., from midpoint to external end 68) is not desired because of the increased potential for fluid communication through the apertures 70 outside the peritoneal cavity 26. It has been found that about 5 to 7 apertures spaced of about 0.3 to 0.8 millimeters in diameter spaced both axially and circumferentially are preferable. The cannula 16 is preferably tapered at its tip 74 to facilitate its introduction through the incision 42 and the puncture in the peritoneum 24 made by the stylet or trocar 48. The tapering also facilitates passage of the cannula 16 in between organs 28 in the peritoneal cavity 26. The cannula 16 is preferably made of a plastic-like material which desirably may be a teflon or silastic substance. The cannula 16 is sized in length to extend well into the peritoneal cavity 26 (e.g., from about 10 to 30 centimeters) after being fully inserted as illustrated in FIG. 7. The cannula 16 is sized in cross-section to fit slideably over the guide means 14 and to permit good fluid communications there through. It has been found that a cannula 16 having an external diameter from about 1.5 to 4.0 millimeters and a wall thickness of from about 0.1 to 0.5 millimeters is most suitable. It has also been found that the taper of the tip 74 of the cannula 16 should be such as to have the tip 74 fit snuggly, uet slideably, about the guide means 14. Cook, Incorporated "dialators" are available which may be used as the above-described cannula 16 after forming the required apertures therein.

The cannula 16 is advanced along the guide means 14 into the cavity 26 until fully inserted with the connector means 66 remaining external to the skin surface 18. The tip 74 of the cannula 16 is thus advanced along the guide means 14 down into the cavity 26 between the organs 28 without extensive resistance and without a significant likelihood of inducing any trauma to the internal organs 28. The guide means 14 is then removed and fluid operation means connected to the connector means 66.

Preferably an aspirator which may be a syringe or a mechanical motor driven type 76 is first connected to the connector means 66 and a suction or vacuum created to extract any fluids present in the cavity 26. The extraction of certain fluids which may be identified either visually or by chemical analysis (e.g., blood) may be sufficient for a treating physician to complete a diagnosis.

If no fluids are extracted by aspiration, then a solution (e.g., a balanced salt solution such as Ringer's Lactate) may be introduced into the cavity 26 by connection to the connector means 66. The volume introduced will vary based on patient size with a typical adult receiving about 1 liter. In some cases, it may then be desirable to employ mixing techniques to cause the solution to mix or wash the internal organs 28. One such technique involves a slow and gentle rocking of the patient from side to side while in the supine position.

Before connecting and introducing the solution, it is preferred to secure the cannula 16 in place with suture 80 and needle 81. That is, the suture 80 is stitched into the skin 18 and tied about the cannula 16 with a knot 82. In this way this cannula 16 is made sufficiently secure so that it will not become dislodged during subsequent fluid operations.

After introduction of the fluid, and mixing if desired, the fluid is extracted. The aspirator 76 may be used. However, frequently it is preferable to not disconnect the fluid container 78 after introduction of the fluid and simply lower the container 78 below the level of the peritoneal cavity 26 to establish a siphon between the cavity 26 and the container 78. The fluid will then return to the container for analysis by the treating physician.

After the fluid is substantially removed, the cannula 16 is removed from the patient and the incision 42 closed with conventional medical dressings or bandages in accordance with standard medical practice.

It should be noted that the apparatus above-described is useful as a diagnostic aid in diagnosing the extent of blunt trauma to the peritoneum and organs within the peritoneal cavity. As such it is useful in an emergency room environment in treating emergency trauma victims. Speed in diagnosing internal injuries is often critical so that life saving repairs (e.g., surgery) can be rapidly effected. To facilitate speed and in turn diagnosis it has been found to be particularly useful to have all the necessary apparatus prepositioned in a ready accessible and easy to use form. Assembling all such material in a prepositioned kit or package is regarded as most useful as it avoids the delay and potential disaster that results when it is discovered that one or more items are not instantly available.

As illustrated in FIG. 1, a preferred package is openable and sealed and contains the intravascular catheter 12, guide means 14 and elongated cannula 16 in their respective individual packages 90, 92 and 94. The individual packages 90, 92 and 94 preferably have at least one transparent side through which the contents can be seen and visually identified which is indicated by the dotted lines 96, 98 and 100. The package 10 also has at least one transparent side as indicated by the dotted line 102.

The package 10 may also contain other items used such as the body drape 32, sponges 30 with preparation solution impregnated, a surgical knife 40, a syringe 36 with needle 38, a local anesthetic 104 and a suture 80 and needle 81. Except for the anesthetic bottle 104, each of these items is preferably individually packaged in its own respective package 106, 108, 110, 112 and 114 which has at least one transparent side through which its contents can be seen and visually identified as indicated by the dotted lines 118, 120, 122 and 124.

Although all the materials and apparatus can be placed in one package, it is regarded as most preferred to place the catheter 12, wire guide 14 and cannula 16 in a one half 10a, and the drape 32, sponges 30, syringe 36 and needle 38, anesthetic 104, knife 40 and suture 80 and needle 81 in a second half 10b of package 10. The two halves 10a, 10b are each separately sealed and openable and separable from each other by tearing along a perforation indicated by the broken line 130. Thus the materials for peritoneal fluid treatment are assembled into one kit ready for instant use. The package 10 can be unitarily stored and transported and separated into its halves 10a, 10b for ease of use, by the physician opening each half and individual packages in order of use to minimize exposure to the environment and potential loss of sterility by the contents.

It should be noted that all items and apparatus are to be sterilized and sterilly packaged in accordance with good medical practice and procedures known to those skilled in the art. Similarly, performance of the method herein disclosed should be effected using sterile techniques in accordance with generally accepted good medical practices.

Although the method apparatus and packages above-described are particularly useful in performing peritoneal lavage for diagnosing blunt abdominal injuries, it is to be understood that the apparatus methods and packages are equally useful for most fluid treatments involving the peritoneal cavity including peritoneal aspiration and peritoneal dialysis.

It is to be understood that the embodiments of the invention and methods disclosed above are merely illustrative of the application of the principles of the inventions. Reference herein to details in steps or apparatus is not intended to limit the scope of the claims which themselves recite those features regarded as essential to the invention.

We claim:

1. A method for peritoneal fluid treatment in which:
   a portion of the skin surface about the peritoneum is sterilized using skin preparation means;
   a local anesthetic is administered to said sterilized skin surface;
   a short, small, shallow incision is made in the area of said sterilized skin;
   an intravascular catheter of the type having a first cannula connected to a hub and removable placement means is inserted through said incision and into the peritoneal cavity;
   the placement means of said intravascular catheter is removed and said first cannula left inserted;
   flexible guide means are inserted into the peritoneal cavity through said first cannula;
   said first cannula is removed leaving said guide means inserted;
   a second cannula which is elongated and flexible is inserted into the peritoneal cavity over said guide means;
   said guide means is removed; and
   fluid operation means is connected to said second cannula by connector means adapted to one end of said cannula to effect fluid treatment operations.

2. The method of claim 1 wherein said second cannula is secured in place by suture means before performance of fluid operations in which fluids are introduced and thereafter extracted from the peritoneal cavity.

3. A method for peritoneal fluid treatment in which:
   a portion of the skin surface about the peritoneum is sterilized using skin preparation means;
   a local anesthetic is administered to said sterilized skin surface;
   a nick-type incision is made in the area of said sterilized skin using incision means;
   a hollow first cannula is placed through said incision and just slightly into the peritoneal cavity;
   flexible guide means is inserted into the peritoneal cavity through said first cannula well into said cavity, said guide means being from about 20 to about 50 centimeters in length and from about 0.5 millimeters to about 2 millimeters in diameter for insertion into the peritoneal cavity through said first cannula, said guide means being sized in cross-section to fit within said first cannula and in length to be substantially longer than said first cannula, said guide means having a first end which is blunt for insertion into the peritoneal cavity, and said guide means being a stainless steel piano-wire-like wire made of a refractory metal having substantial flexibility from its first end to a point from about one-third to one-half the length of said guide means measured from said first end and thereafter said guide means has less flexibility along its length to its second end;

said first cannula is removed leaving said guide meams inserted;

a second cannula which is elongated and flexible is inserted into the peritoneal cavity over said guide means, said second cannula being a flexible plastic-like tube having a plurality of spaced apart apertures formed in it from its second end to a point about one-third to one-half along its length and secured in placed by suture means before performance of fluid operations in which fluids are introduced and thereafter extracted from the peritoneal cavity;

said guide means is removed; and fluid operation means is connected to said second cannula by connector means adapted to one end of said cannula to effect fluid treatment operations.

4. The method of claim 3 wherein said fluid operation means is a fluid container connectable by means to said connector means, said fluid container having a first position in which said container is elevated above the connector so that fluid therewithin flows out into the patient, and a second position in which said container is lowered below the patient to establish a siphon and extract fluid from the patient into the container.

5. The method of claim 3 wherein said peritoneal fluid operation means includes an aspirator connectable to said connector means to extract fluid from said patient.

6. A method for peritoneal fluid treatment in which:

a portion of the skin surface about the peritoneum is prepared for incision making;

a local anesthetic is selectively administered to the prepared skin surface;

a small incision is made within the prepared skin surface area;

a hollow first cannula is placed through the incision and just slightly into the peritoneal cavity;

flexible guide means is inserted into the peritoneal cavity, said guide means being sized in cross-section to fit within said first cannula and in length to be substantially longer than said first cannula;

said first cannula is removed leaving said guide means inserted;

a second cannula which is elongated and flexible is inserted into the peritoneal cavity over the guide means;

said second cannula is selectively secured in place using securing means;

said guide means is removed; and fluid operation means is connected to said second cannula by connector means to effect fluid treatment operations.

* * * * *